United States Patent
Raffy et al.

(10) Patent No.: US 11,868,613 B1
(45) Date of Patent: Jan. 9, 2024

(54) SELECTION OF HEALTH CARE DATA STORAGE POLICY BASED ON HISTORICAL DATA STORAGE PATTERNS AND/OR PATIENT CHARACTERISTICS USING AN ARTIFICIAL INTELLIGENCE ENGINE

(71) Applicant: Change Healthcare Holdings LLC, Nashville, TN (US)

(72) Inventors: Philippe Raffy, Edina, MN (US); Jean-Francois Pambrun, La Prairie (CA); David Dubois, Mirabel (CA); Ashish Kumar, Danville, CA (US)

(73) Assignee: CHANGE HEALTHCARE HOLDINGS LLC, Nashville, TN (US)

( * ) Notice: Subject to any disclaimer, the term of this patent is extended or adjusted under 35 U.S.C. 154(b) by 304 days.

(21) Appl. No.: 17/150,364

(22) Filed: Jan. 15, 2021

(51) Int. Cl.
| | |
|---|---|
| *G06F 3/06* | (2006.01) |
| *G06N 20/00* | (2019.01) |
| *G16H 10/60* | (2018.01) |
| *G06F 18/2415* | (2023.01) |
| *G06F 18/2413* | (2023.01) |

(52) U.S. Cl.
CPC .......... *G06F 3/0604* (2013.01); *G06F 3/0608* (2013.01); *G06F 3/0643* (2013.01); *G06F 18/2415* (2023.01); *G06F 18/24147* (2023.01); *G06N 20/00* (2019.01); *G16H 10/60* (2018.01); *G06F 3/0683* (2013.01)

(58) Field of Classification Search
CPC .......... G06F 3/0604; G06G 18/24147; G06N 20/00; G16H 10/60
See application file for complete search history.

(56) References Cited

U.S. PATENT DOCUMENTS

| | | | |
|---|---|---|---|
| 8,112,586 B1 * | 2/2012 | Reiner | H04L 67/2885 711/119 |
| 2018/0101547 A1 * | 4/2018 | Greenfield | G06F 16/2228 |
| 2020/0210867 A1 * | 7/2020 | Banis | G06N 5/04 |
| 2021/0383197 A1 * | 12/2021 | Da Silva | G06N 3/063 |
| 2022/0180744 A1 * | 6/2022 | Zou | G06F 18/295 |

\* cited by examiner

*Primary Examiner* — Baboucarr Faal
(74) *Attorney, Agent, or Firm* — Myers Bigel, P.A.

(57) ABSTRACT

A method includes defining a plurality of data storage policies, each of the plurality of data storage policies providing rules for storing data among a plurality of data storage locations, each of the plurality of data storage locations having a data storage cost and a data retrieval cost associated therewith; determining a baseline policy distribution among the plurality of data storage policies for an entity; receiving new data items corresponding to the entity; storing the new data items in the plurality of data storage locations using the plurality of data storage policies based on the baseline policy distribution; and determining, using the artificial intelligence engine, a selected one of the plurality of data storage policies to use in storing the new data items corresponding to the entity based on the data storage cost for each of the plurality of data storage locations, and the data retrieval cost for each of the plurality of storage locations.

20 Claims, 7 Drawing Sheets

SELECTION OF HEALTH CARE DATA STORAGE POLICY BASED ON HISTORICAL DATA STORAGE PATTERNS AND/OR PATIENT CHARACTERISTICS USING AN ARTIFICIAL INTELLIGENCE ENGINE

FIELD

The present inventive concepts relate generally to health care systems and services and, more particularly, to artificial intelligence systems that can be used by health care providers for determining how to store health care data, such as images.

BACKGROUND

Health care service providers manage and store a variety of different types of personal healthcare information (PHI) for patients. One type of information is imaging data sets resulting from various types of imaging applications, such as X-ray, magnetic resonance imaging (MRI), computed tomography (CT), and the like. Due to their size, however, image data sets can be expensive to store due to the amount of storage space they may consume. As a result, health care service providers may make use of a variety of different storage locations to store image datasets, such as online and offline storage. Health care service providers may develop policies or rules that govern where a particular image is stored. For example, an x-ray for a child may be stored in online storage for three months and then moved to offline storage. A head CT on a child may be stored in online storage for six weeks and then moved to offline storage unless the child has had two or more CT in the past. In this case, the child's CT will remain in online storage for six months. A mammogram that is associated with a negative result may be moved to offline storage immediately and then retrieved to online storage at the patient's appointment the following year.

These policies or rules may, however, become outdated or be inapplicable over time. The policies may also vary from one health care facility to another. Thus, a health care facility may not benefit from best practices that have been developed in the industry for the storage of imaging data.

SUMMARY

According to some embodiments of the inventive concept, a method comprises defining a plurality of data storage policies, each of the plurality of data storage policies providing rules for storing data among a plurality of data storage locations, each of the plurality of data storage locations having a data storage cost and a data retrieval cost associated therewith; determining a baseline policy distribution among the plurality of data storage policies for an entity; receiving new data items corresponding to the entity; storing the new data items in the plurality of data storage locations using the plurality of data storage policies based on the baseline policy distribution; and determining, using the artificial intelligence engine, a selected one of the plurality of data storage policies to use in storing the new data items corresponding to the entity based on the data storage cost for each of the plurality of data storage locations, and the data retrieval cost for each of the plurality of storage locations.

In other embodiments the method further comprises evaluating a new data item storage metric for the new data items. Determining, using the artificial intelligence engine, a selected one of the plurality of data storage policies to use in storing the new data items corresponding to the entity comprises determining, using the artificial intelligence engine, a selected one of the plurality of data storage policies to use in storing the new data items corresponding to the entity based on the new data item storage metric, the data storage cost for each of the plurality of data storage locations, and the data retrieval cost for each of the plurality of storage locations.

In still other embodiments, evaluating the new data item storage metric for the new data items comprises determining frequency of access for the new data items from the plurality of data storage locations.

In still other embodiments, the baseline policy distribution among the plurality of data storage policies for the entity is a uniform policy distribution among the plurality of data storage policies.

In still other embodiments, determining the baseline policy distribution among the plurality of data storage policies for the entity comprises determining a historical distribution of the plurality of storage policies for storing historical data items corresponding to the entity.

In still other embodiments, determining the historical distribution of the plurality of storage policies for storing historical data items corresponding to the entity comprises assigning the historical data items to ones of the plurality of storage policies using a multi-arm bandit allocation process based on the data storage cost for each of the plurality of data storage locations and the data retrieval cost for each of the plurality of storage locations.

In still other embodiments, a sum of the data storage costs and the data retrieval costs for the plurality of data storage locations associated with the selected one of the plurality of data storage policies is less than or equal to a sum of the data storage costs and the data retrieval costs for the plurality of data storage locations associated with other ones of the plurality of data storage policies, respectively.

In still other embodiments, the entity is a patient and the new data items comprise new health care data items. The method further comprises receiving information associated with the patient; and identifying features in the information associated with the patient that are predictive of a frequency of access for the new data items.

In still other embodiments, the method further comprises receiving labels for the information associated with the patient, the labels corresponding to frequency of access categories for the new data items.

In still other embodiments, identifying the features in the information associated with the patient comprises identifying the features by applying a clustering technique to the information associated with the patient; or identifying the features by applying a stepwise regression technique to the information associated with the patient.

In still other embodiments, determining, using the artificial intelligence engine, the selected one of the plurality of data storage policies to use in storing the new data items corresponding to the patient comprises determining, using the artificial intelligence engine, the selected one of the plurality of data storage policies to use in storing the new data items corresponding to the by applying a modeling technique to the features in the information associated with the patient and the labels received for the information associated with the patient.

In still other embodiments, the modeling technique comprises a multi-arm bandit technique, a regression technique, a neural network technique, an Autoregressive Integrated Moving Average (ARIMA) technique, a deep learning technique, a linear discriminant analysis technique, a decision tree technique, a naïve Bayes technique, a K-nearest neighbors technique, a learning vector quantization technique, a support vector machine technique, and/or a bagging/random forest technique.

In still other embodiments, the information associated with the patient comprises an age, a gender, a problem list, an encounter diagnosis, a patient class, and/or a medical center department.

In still other embodiments, the plurality of data storage locations comprises an online storage location, a nearline storage location, and a coldline storage location.

In some embodiments of the inventive concept, a system comprises a processor and a memory coupled to the processor and comprising computer readable program code embodied in the memory that is executable by the processor to perform operations comprising defining a plurality of data storage policies, each of the plurality of data storage policies providing rules for storing data among a plurality of data storage locations, each of the plurality of data storage locations having a data storage cost and a data retrieval cost associated therewith; determining a baseline policy distribution among the plurality of data storage policies for an entity; receiving new data items corresponding to the entity; storing the new data items in the plurality of data storage locations using the plurality of data storage policies based on the baseline policy distribution; and determining, using the artificial intelligence engine, a selected one of the plurality of data storage policies to use in storing the new data items corresponding to the entity based on the data storage cost for each of the plurality of data storage locations, and the data retrieval cost for each of the plurality of storage locations.

In further embodiments, the entity is a patient and the new data items comprise new health care data items. The operations further comprise receiving information associated with the patient; and identifying features in the information associated with the patient that are predictive of the frequency of access for the new data items.

In still further embodiments, the operations further comprise receiving labels for the information associated with the patient, the labels corresponding to frequency of access categories for the new data items.

In still further embodiments, identifying the features in the information associated with the patient comprises identifying the features by applying a clustering technique to the information associated with the patient; or identifying the features by applying a stepwise regression technique to the information associated with the patient.

In some embodiments of the inventive concept, a computer program product comprises a non-transitory computer readable storage medium comprising computer readable program code embodied in the medium that is executable by a processor to perform operations comprising defining a plurality of data storage policies, each of the plurality of data storage policies providing rules for storing data among a plurality of data storage locations, each of the plurality of data storage locations having a data storage cost and a data retrieval cost associated therewith; determining a baseline policy distribution among the plurality of data storage policies for an entity; receiving new data items corresponding to the entity; storing the new data items in the plurality of data storage locations using the plurality of data storage policies based on the baseline policy distribution; and determining, using the artificial intelligence engine, a selected one of the plurality of data storage policies to use in storing the new data items corresponding to the entity based on the data storage cost for each of the plurality of data storage locations, and the data retrieval cost for each of the plurality of storage locations.

In other embodiments, the entity is a patient and the new data items comprise new health care data items. The operations further comprise receiving information associated with the patient; and identifying features in the information associated with the patient that are predictive of the frequency of access for the new data items.

Other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter, and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

In the following detailed description, numerous specific details are set forth to provide a thorough understanding of embodiments of the present inventive concept. However, it will be understood by those skilled in the art that the present invention may be practiced without these specific details. In some instances, well-known methods, procedures, components and circuits have not been described in detail so as not to obscure the present inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

Embodiments of the inventive concept are described herein in the context of a prediction engine that includes a machine learning engine and an artificial intelligence (AI) engine. It will be understood that embodiments of the inventive concept are not limited to a machine learning implementation of the prediction engine and other types of AI systems may be used including, but not limited to, a multi-layer neural network, a deep learning system, a natural language processing system, and/or computer vision system. Moreover, it will be understood that the multi-layer neural network is a multi-layer artificial neural network comprising artificial neurons or nodes and does not include a biological neural network comprising real biological neurons.

Embodiments of the inventive concept are described herein in the context of using an AI assisted data storage policy selection system to select a policy for storing health care data items, such as imaging data items. It will be understood, however, that embodiments of the inventive concept are not limited to the application of storing health care imaging data items, but may also be used for selecting a storage policy for storing other types of health care and non-health care data items.

Some embodiments of the inventive concept stem from a realization that health care service providers, for example, are responsible for managing and storing large amounts of personal healthcare information (PHI). This PHI may include, for example, imaging data sets or data items that may consume large amounts of storage. As a result, health care service providers may make use of multiple storage locations and develop policies that include rules for selecting a particular storage location for a particular data item, e.g., imaging data item. These rules may attempt to balance the cost of storage against the cost of retrieval based on a data storage item metric, such as, for example, an expected frequency of access of the various data items. These policies and rules, may, however, become outdated, break, or otherwise fall far short of optimizing the cost of storage and the cost of data retrieval. Some embodiments of the inventive concept may provide an AI assisted data storage policy selection system that may determine a baseline policy distribution used, for example, by a health care service provider in storing data items and then use an AI engine to learn a health care service provider's data usage over time based on the use of various data storage policies to determine a particular policy that may improve a key performance index/indicator (KPI), which may be defined as a sum of the cost of storage and the cost of data retrieval. In some embodiments, the data storage policy selection may be individualized on a per-patient basis, such that the KPI may be improved for that patient's particular data item generation and usage. The AI assisted data storage policy selection system may make further use of patient characteristics in determining a particular data storage policy for that patient's data. For example, the AI assisted data storage policy selection system may incorporate patient characteristics, such as age, gender, problem list, encounter diagnosis, patient class, and/or medical center department visited in selecting a data storage policy as these characteristics may be indicative to the data item storage metric, such as a frequency of access of data items, associated with the patient. Thus, the AI assisted data storage policy selection system may help a health care service provider to use its data storage policies in an improved manner that is adaptable over time. As new policies become inapplicable or break, they may not be selected for storage of a patient's data and can be removed or modified to improve their effectiveness. Moreover, a data storage policy may be selected and applied on a per patient basis, such that the data storage policy selection is made for each patient based on that patient's characteristics and/or data item storage metric. This may improve the overall KPI for the health care service provider relative to applying a particular policy to groups of patients or categories of patients.

Figure 1:
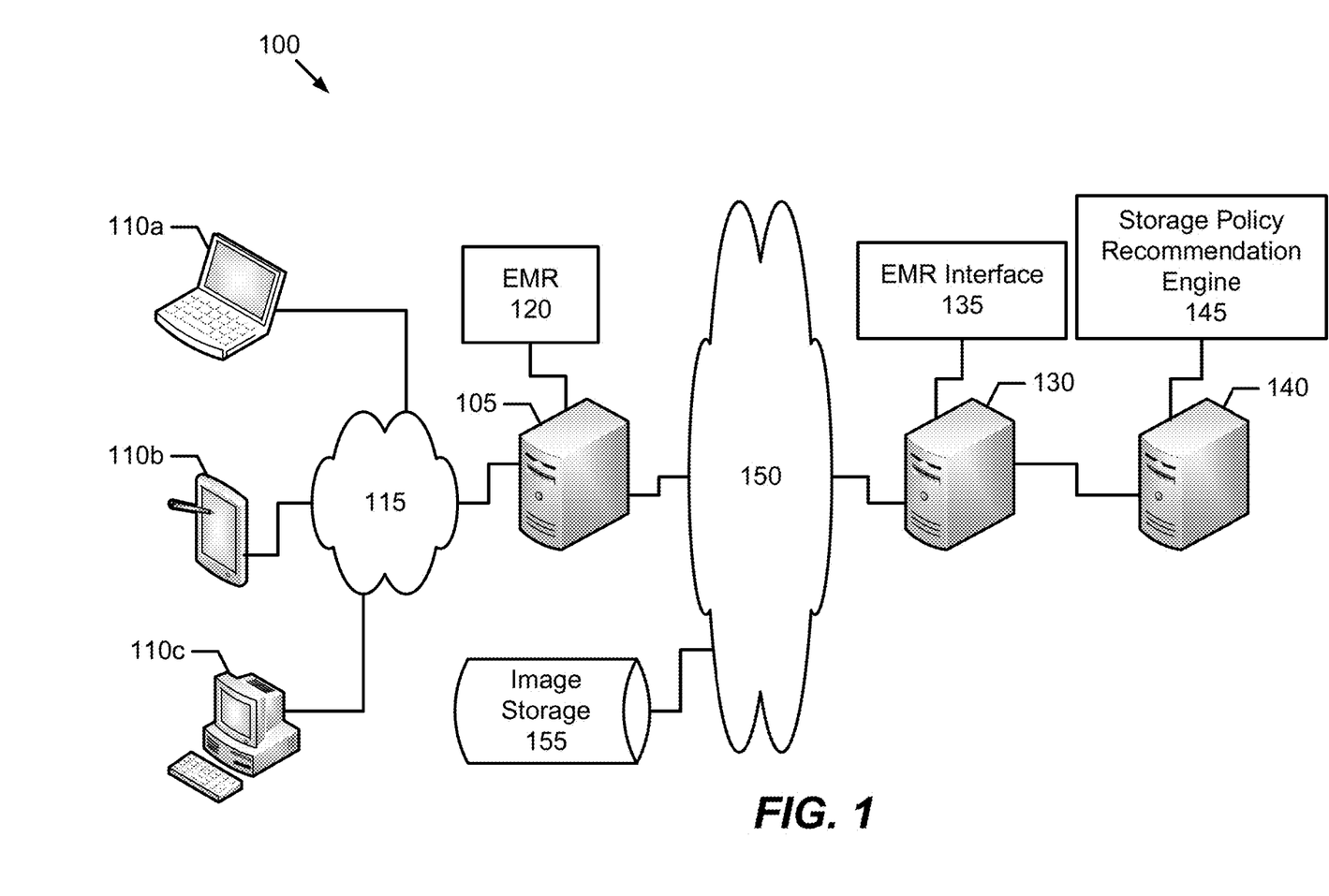
FIG. 1 is a block diagram that illustrates a communication network including an Artificial Intelligence (AI) assisted data storage policy selection system in accordance with some embodiments of the inventive concept.

Referring to FIG. 1, a communication network 100 including an AI assisted data storage policy selection system, in accordance with some embodiments of the inventive concept, comprises a health care facility server 105 that is coupled to devices 110a, 110b, and 110c via a network 115. The health care facility may be any type of health care or medical facility, such as a hospital, doctor's office, specialty center (e.g., surgical center, orthopedic center, laboratory center etc.), or the like. The health care facility server 105 may be configured with an Electronic Medical Record (EMR) system module 120 to manage patient files and facilitate the entry of orders for patients via health care service providers ("providers"). Although shown as one combined system in FIG. 1, it will be understood that some health care facilities use separate systems for electronic medical record management and order entry management. The providers may use devices, such as devices 110a, 110b, and 110c to manage patients' electronic records and to issue orders for the patients through the EMR system 120. An order may include, but is not limited to, a treatment, a procedure (e.g., surgical procedure, physical therapy procedure, radiologic/imaging procedure, etc.) a test, a prescription, and the like. The network 115 communicatively couples the devices 110a, 110b, and 110c to the health care facility server 105. The network 115 may comprise one or more local or wireless networks to communicate with the health care facility server 105 when the health care facility server 105 is located in or proximate to the health care facility. When the health care facility server 105 is in a remote location from the health care facility, such as part of a cloud computing system or at a central computing center, then the network 115 may include one or more wide area or global networks, such as the Internet.

Figure 2:
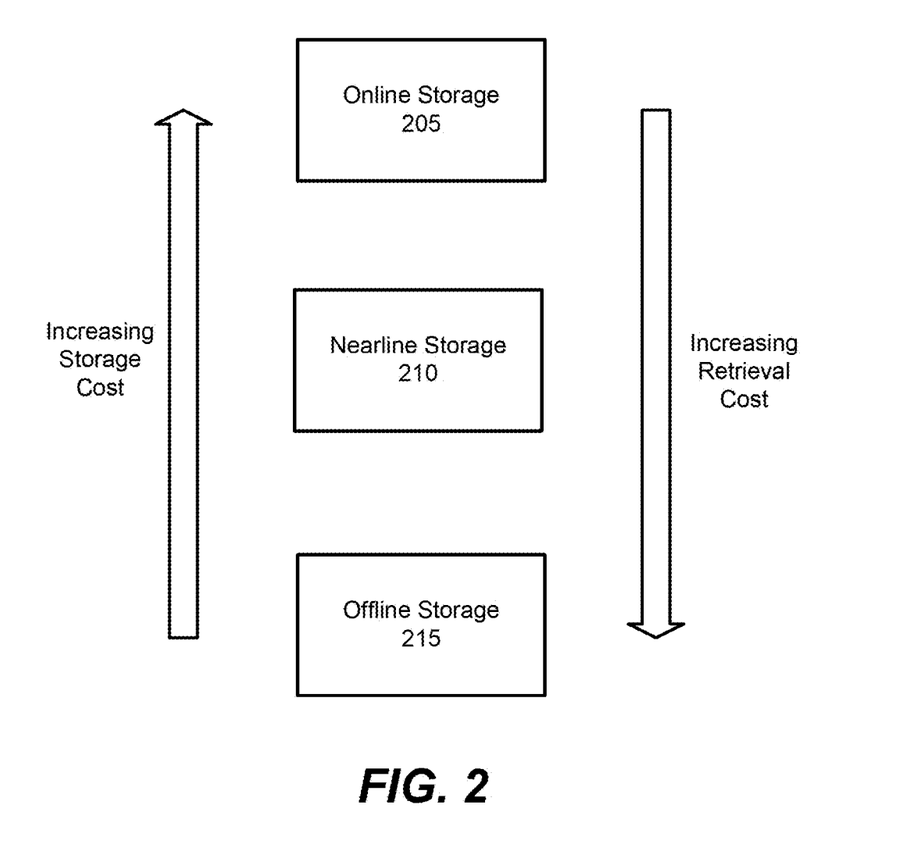
FIG. 2 is a block diagram that illustrates the relationship between different data storage locations in accordance with some embodiments of the inventive concept.

According to some embodiments of the inventive concept, providers may access an AI assisted data storage policy selection system to assist the provider in selecting a policy for storing data items associated with a patient, such as storing imaging data items, in the image storage facility 155. The image storage facility 155 may be representative of a plurality of data storage locations that may be used to store patient data, which may be, for example, image data items. The image storage facility 155 may be illustrated by way of example with reference to FIG. 2. As shown in the FIG. 2 example, the data storage facility may include three different data storage locations: an online storage location 205, a nearline storage location 210, and an offline storage location 215. The online storage location 205 may be used for patient images that are typically accessed within three months. The nearline storage location 210 may be used for patient images that are typically accessed every three to six months. And the offline storage location 215 may be used for patient images that typically go more than six months between being accessed. As shown in FIG. 2, the cost of storage is inversely related to the cost of retrieval with respect to the online storage location 205, the nearline storage location 210, and the offline storage location 215.

Returning to FIG. 1, the AI assisted data storage policy selection system may include a health care facility interface server 130, which includes an EMR interface module 135 to facilitate the transfer of information between the EMR system 120, which the providers use to manage patient records and issue orders, and an AI server 140, which includes a storage policy recommendation engine module 145. The AI server 140 and storage policy recommendation engine module 145 may be configured to receive patient information, contained in records in the EMR system 120 along with provider storage policy information from the health care facility server 105 and EMR system module 120 by way of the health care facility interface server 130 and EMR interface module 135. The EMR interface module 135 in conjunction with the storage policy recommendation engine module 145 may be further configured to generate a recommendation or selection of a data storage policy from among a plurality of data storage policies available to a provider to use for storing data items associated with a patient, such as imaging data items or data sets. It will be understood that the division of functionality described herein between the AI server 140/storage policy recommendation engine module 145 and the health care facility interface server 130/EMR interface module 135 is an example. Various functionality and capabilities can be moved between the AI server 140/storage policy recommendation engine module 145 and the health care facility interface server 130/EMR interface module 135 in accordance with different embodiments of the inventive concept. Moreover, in some embodiments, the AI server 140/storage policy recommendation engine module 145 and the health care facility interface server 130/EMR interface module 135 may be merged as a single logical and/or physical entity.

A network 150 couples the health care facility server 105 to the health care facility interface server 130. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The service provided through the health care facility interface server 130, EMR interface module 135, AI server 140 and storage policy recommendation engine module 145 to provide AI assisted data storage policy selection may, in some embodiments, be embodied as a cloud service. For example, health care facilities may integrate their EMR systems/order systems with the AI assisted data storage policy selection service and access the service as a Web service. In some embodiments, the AI assisted data storage policy selection service may be implemented as a Representational State Transfer Web Service (RESTful Web service).

Although FIG. 1 illustrates an example communication network including an AI assisted data storage policy selection system, it will be understood that embodiments of the inventive concept are not limited to such configurations, but are intended to encompass any configuration capable of carrying out the operations described herein.

Figure 3:
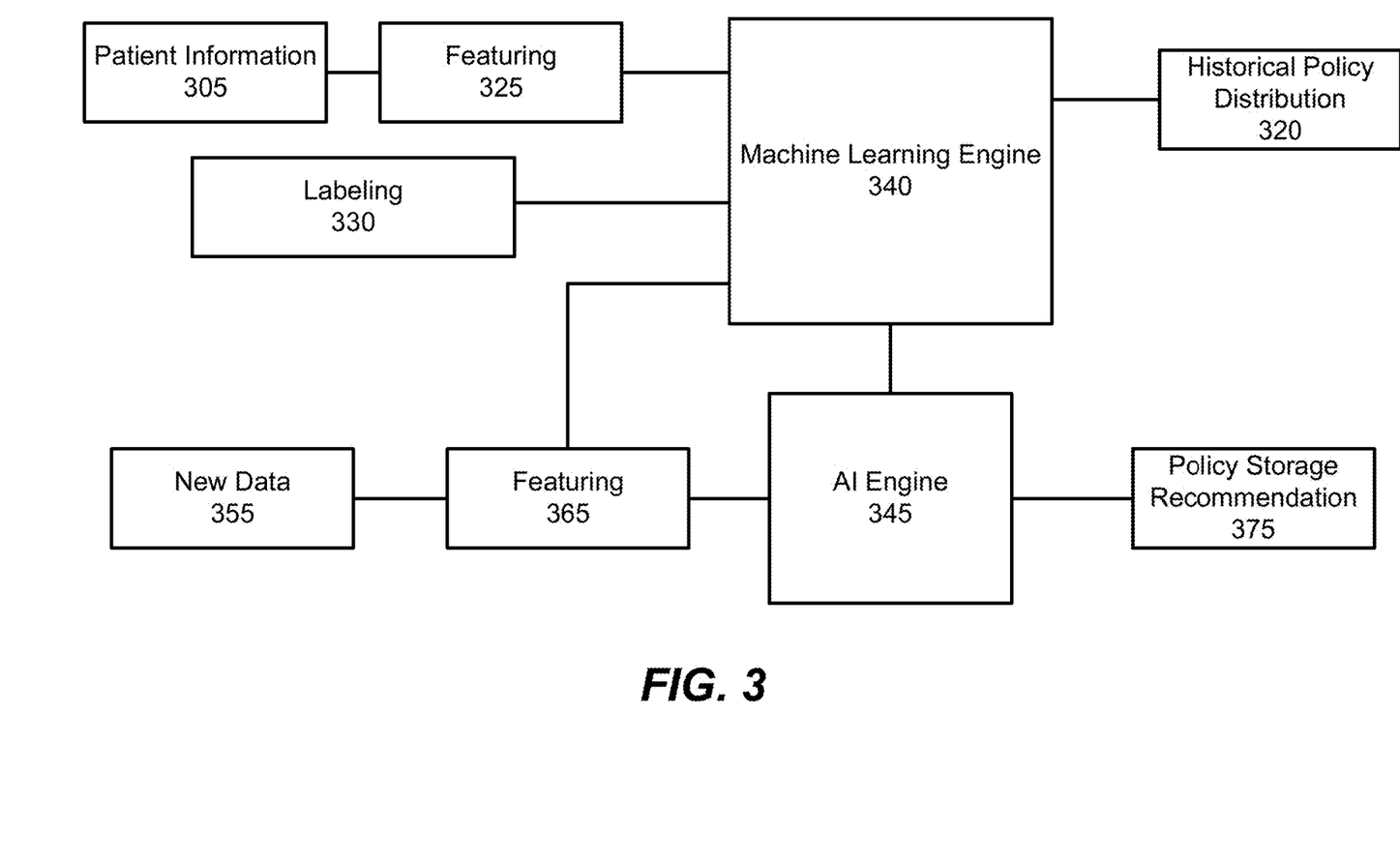
FIG. 3 is a block diagram of the AI assisted data storage policy selection system of FIG. 1 in accordance with some embodiments of the inventive concept.

FIG. 3 is a block diagram of the AI assisted data storage policy selection system of FIG. 1 including the AI server 140 and the storage policy recommendation engine module 145 for providing AI assisted data storage policy selection according to some embodiments of the inventive concept. As shown in FIG. 3, the AI assisted data storage policy selection system may include both training modules and modules used for processing new data on which to make data storage policy selections. The modules used in the training portion of the AI assisted data storage policy selection system include the patient information 305, the featuring module 325, the labeling module 330, the historical policy distribution module 320, and the machine learning engine 340. The patient information 305 may comprise patient demographic and characteristic information that may be predictive of a data item storage metric, such as for example, the frequency of access for the patient's data items from storage. The featuring module 325 is configured to identify the individual independent variables that are used by the AI assisted data storage policy selection system to make a policy selection, which may be considered a dependent variable. For example, the patient information 305 may be generally unprocessed or formatted and include extra information in addition to patient demographic and characteristics information. For example, patient information may include account codes, home address information, and the like, which can be filtered out by the featuring module 325. The features extracted from the patient information 305 may be called attributes and the number of features may be called the dimension. The labeling module 330 may be configured to assign defined labels to the patient information and to the selected data storage policy to ensure a consistent naming convention for both the input features and the generated outputs. The labels may correspond to attributes of a data item storage metric, such as frequency of access categories for data items stored on behalf of the patient. The historical policy distribution module 320 may be configured to determine a baseline distribution of the use of the plurality of data storage policies associated with a health care service provider or facility for respective ones of the provider's patients based on historical data provided by the provider. A multi-arm bandit allocation process may be used to determine the distribution of data storage policies for respective ones of the patients based on the provider's historical data. In some embodiments, when the historical data is unavailable or unreliable, a uniform distribution among the different data storage polices may be used as a default distribution for the baseline distribution. The machine learning engine 340 may process both the featured patient information 305, including the labels provided by the labeling module 330, the baseline policy distribution generated by the historical policy distribution module 320, and storage and retrieval costs information associated with the various data storage locations and may be configured to test numerous functions to establish a quantitative relationship between the featured and labeled input information, baseline data storage policy distribution, and a selected or recommended data storage policy from among the multiple data storage policies available to provider. The machine learning engine 340 may use modeling techniques to evaluate the effects of various input data features on the selected or recommended outputs. These effects may then be used to tune and refine the quantitative relationship between the featured and labeled input data and the selected or recommended data storage policy outputs. The tuned and refined quantitative relationship between the featured and labeled input data and the selected or recommended data storage policy outputs developed by the machine learning engine 340 is output for use in the AI engine 345. The machine learning engine 340 may be referred to as a machine learning algorithm.

The modules used for processing new data on which to make a data storage policy selection include the new data 355, the featuring module 365, the AI engine module 345, and the policy storage selection or recommendation module 375. The new data 355 may be the same data/information as the patient information 305 as well as a request for one or more data items, e.g., one or more images, to be stored in a storage location on behalf of a patient. Likewise, the featuring module 365 performs the same functionality on the new data 355 as the featuring module 325 performs on the patient information 305 including featuring the data items to be stored on behalf of the patient. The AI engine 345 may, in effect, be generated by the machine learning engine 240 in the form of the quantitative relationship determined between the featured and labeled input data and the selected data storage policy that is output. The AI engine 345 may, in some embodiments, be referred to as an AI model. The AI engine 345 may be configured to output selected or recommended data storage policies via the policy storage recommendation or selection module 375. The policy storage recommendation or selection module 375 may be configured to communicate the policy storage selection or recommendation to the provider for approval or may be implemented automatically if the provider chooses. As shown in FIG. 3, the machine learning engine 340 may update the quantitative relationship between the featured and labeled input data and the selected or recommended data storage policy outputs based on the featured patient information and data items to be stored output from the featuring module 365.

Figure 4:
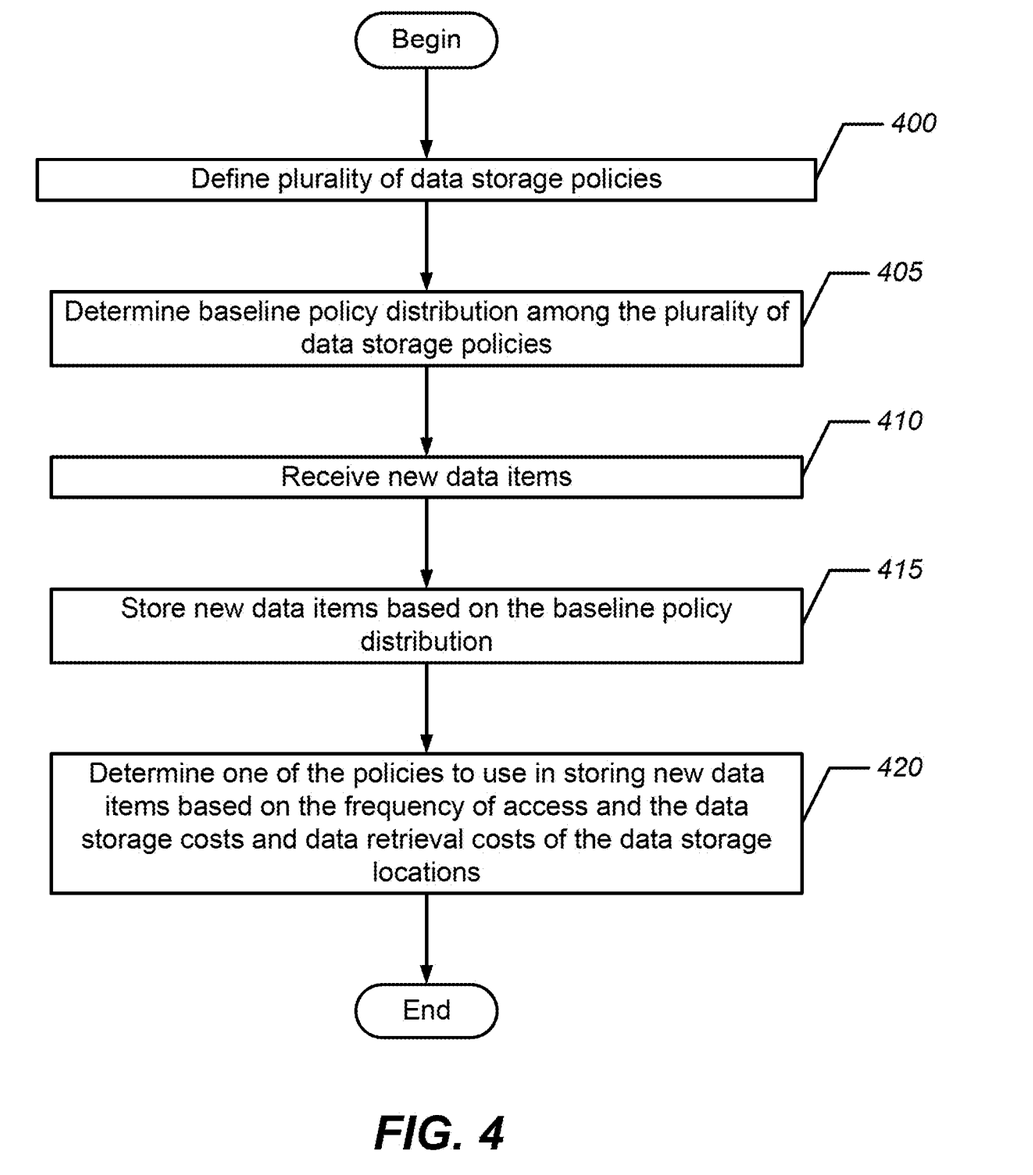
FIGS. 4-5 are flowcharts that illustrate operations for selecting a data storage policy using the AI assisted data storage policy selection system of FIG. 1 in accordance with some embodiments of the inventive concept.
Figure 5:
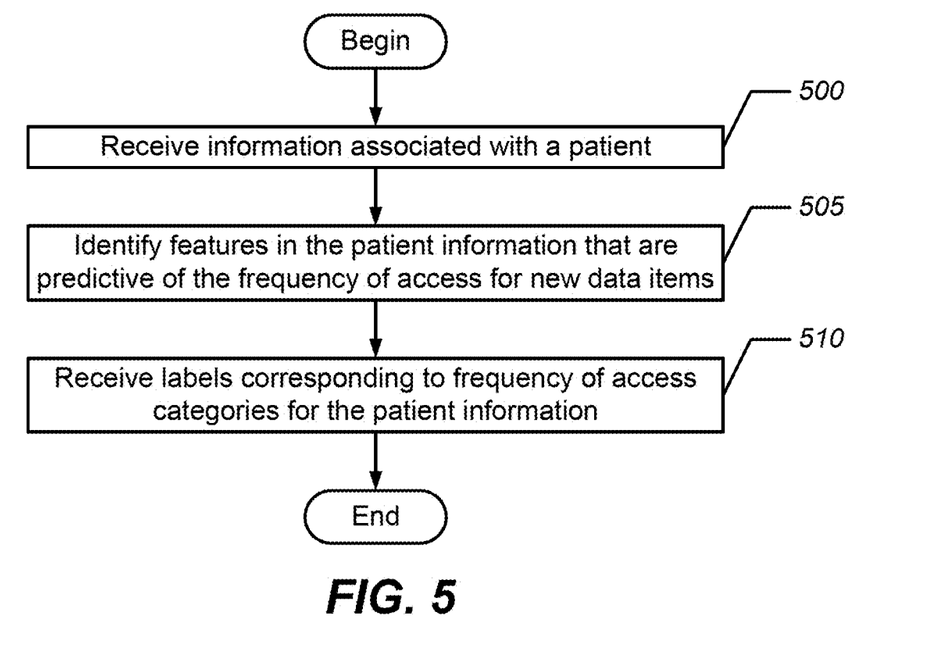

FIGS. 4-5 are flowcharts that illustrate operations for selecting a data storage policy using an AI assisted data storage policy selection system in accordance with some embodiments of the inventive concept. Referring now to FIG. 4, a provider may define a plurality of data storage policies at block 400 for storing patient data items. The policies may include rules specifying destination data storage locations for patient data items, such as image data items or data sets. The data storage locations may have different data storage costs and different data retrieval costs associated therewith. As described above with respect to FIG. 2, these costs may be inversely related. At block 405, the historical policy distribution module 320 may determine a baseline distribution of the data storage policies as used for a particular entity, such as a patient. The baseline distribution may, in some embodiments be defined as a uniform distribution among the plurality of data storage policies. In other embodiments, historical provider data items may be used to determine a historical distribution for the data storage policies using, for example, a multi-arm bandit process.

According to some embodiments of the inventive concept, the AI assisted data storage policy selection system may learn in real-time based on new patient data and data item storage requests. At block 410, new data items are received for an entity, such as a patient, and the new data items may be stored based on the baseline policy distribution at block 415. One of the data storage policies is determined as a selected or recommended data storage policy for the entity or patient at block 420 based on the data storage costs and data retrieval costs associated with the various data storage locations. In some embodiments, the sum of the data storage cost and data retrieval cost for the selected data storage policy may be less than or equal to the sum of the data storage cost and data retrieval cost for other ones of the data storage policies for the entity's or patient's data items. In some embodiments, the determining one of the policies to use in storing new data items may be further based on evaluation of a data item storage metric for the new data items, such as a frequency of access of the new data items in combination with the data storage costs and data retrieval costs of the data storage locations.

In some embodiments of the inventive concept, a modeling technique, such as a multi-arm bandit technique, may be applied to the new data items, a data item storage metric, such as frequency of access information, the data storage costs, and/or the data retrieval costs in determining a selected or recommended data storage policy at block 425.

As described above, the AI assisted data storage policy selection system may be supplemented with additional information regarding an entity or patient. For example, referring to FIG. 5, patient information may be received at block 500, which may include, for example, an age, gender, problem list, encounter diagnosis, patient class, and/or a medical center department where the patient is treated. Features may be identified for the information associated with the patient that are predictive of a new data item storage metric, such as, for example, the frequency of access of new data items for storage that are associated with the patient at block 505. Labels may be received at block 510 corresponding to the new data item storage metric, e.g., frequency of access categories, for the patient information. The features may be identified for the information associated with the patient using various techniques, such as clustering and/or a stepwise regression technique. One of the data storage policies may then be selected for the entity or patient based on the new data item storage metric, e.g., frequency of access of the new data items, the data storage costs and data retrieval costs associated with the various data storage locations, as well as the featured patient information. A modeling technique may be performed on the featured patient information and labels as part of the data storage policy selection. In accordance with some embodiments of the inventive concept, the modeling technique may comprise a multi-arm bandit technique a regression technique, a neural network technique, an Autoregressive Integrated Moving Average (ARIMA) technique, a deep learning technique, a linear discriminant analysis technique, a decision tree technique, a naïve Bayes technique, a K-nearest neighbors technique, a learning vector quantization technique, a support vector machine technique, and/or a bagging/random forest technique.

Figure 6:
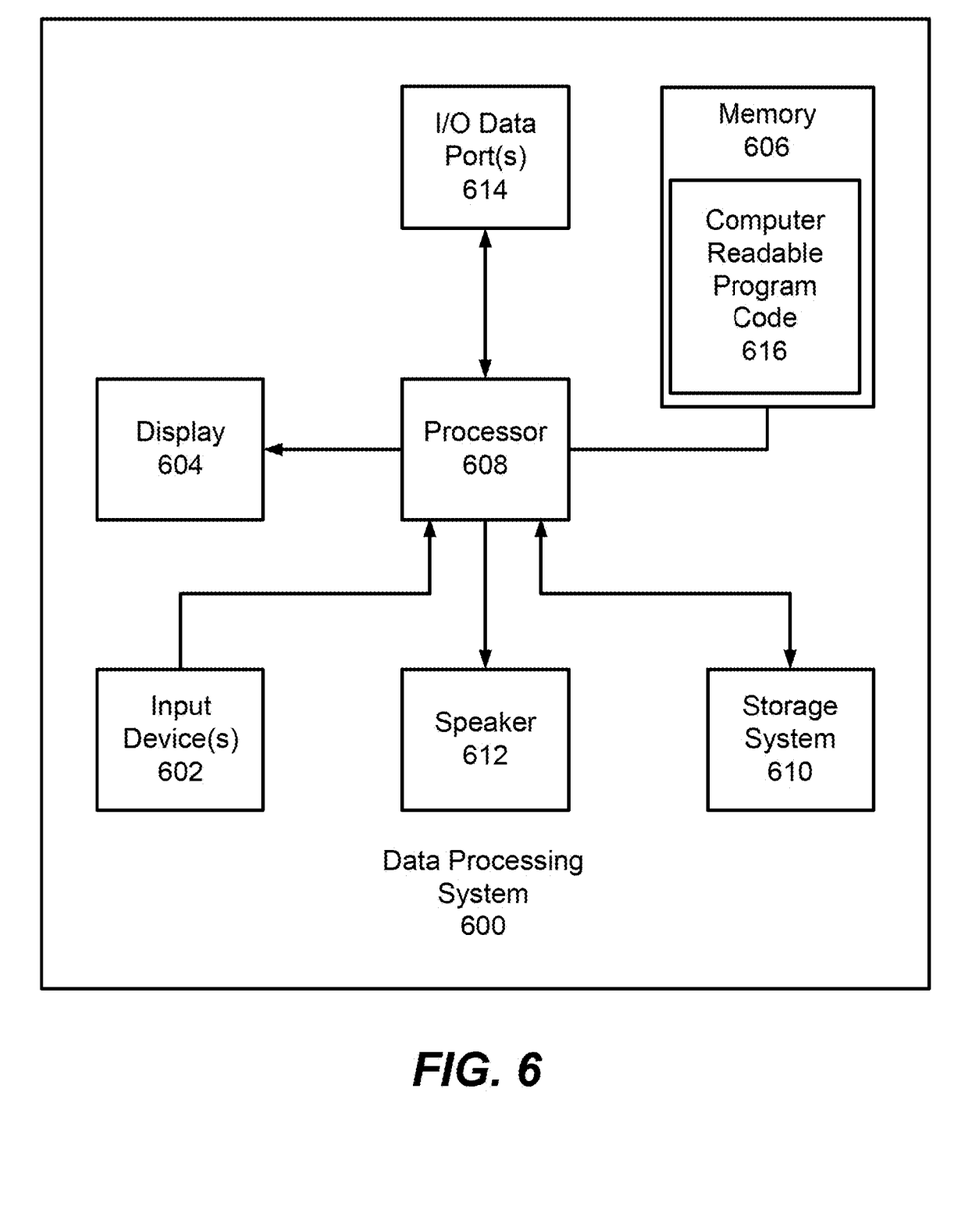
FIG. 6 is a data processing system that may be used to implement one or more servers in the AI assisted data storage policy selection system of FIG. 1 in accordance with some embodiments of the inventive concept.

Referring now to FIG. 6, a data processing system 600 that may be used to implement the AI server 140 of FIG. 1, in accordance with some embodiments of the inventive concept, comprises input device(s) 602, such as a keyboard or keypad, a display 604, and a memory 606 that communicate with a processor 608. The data processing system 600 may further include a storage system 610, a speaker 612, and an input/output (I/O) data port(s) 614 that also communicate with the processor 608. The processor 608 may be, for example, a commercially available or custom microprocessor. The storage system 610 may include removable and/or fixed media, such as floppy disks, ZIP drives, hard disks, or the like, as well as virtual storage, such as a RAMDISK. The I/O data port(s) 1114 may be used to transfer information between the data processing system 600 and another computer system or a network (e.g., the Internet). These components may be conventional components, such as those used in many conventional computing devices, and their functionality, with respect to conventional operations, is generally known to those skilled in the art. The memory 606 may be configured with computer readable program code 616 to facilitate AI assisted data storage policy selection according to some embodiments of the inventive concept.

Figure 7:
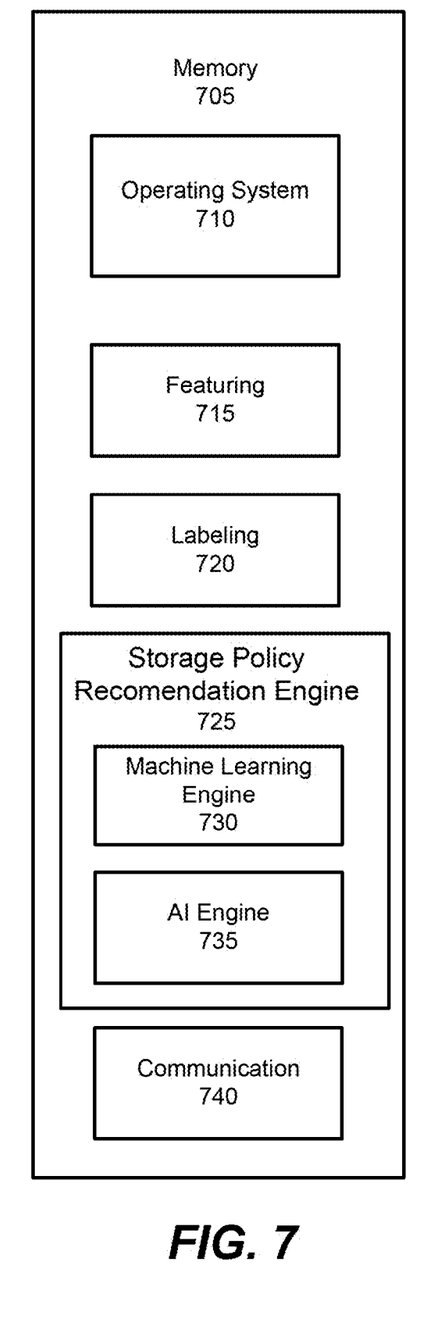
FIG. 7 is a block diagram that illustrates a software/hardware architecture for use in the AI assisted data storage policy selection system of FIG. 1 in accordance with some embodiments of the inventive concept.

FIG. 7 illustrates a memory 705 that may be used in embodiments of data processing systems, such as the AI server 140 of FIG. 1 and the data processing system 600 of FIG. 6, respectively, to facilitate AI assisted data storage policy selection according to some embodiments of the inventive concept. The memory 705 is representative of the one or more memory devices containing the software and data used for facilitating operations of the AI server 140 and storage policy recommendation engine 145 as described herein. The memory 705 may include, but is not limited to, the following types of devices: cache, ROM, PROM, EPROM, EEPROM, flash, SRAM, and DRAM. As shown in FIG. 7, the memory 705 may contain five or more categories of software and/or data: an operating system 710, a featuring module 715, a labeling module 720, a storage policy recommendation engine module 725, and a communication module 740. In particular, the operating system 710 may manage the data processing system's software and/or hardware resources and may coordinate execution of programs by the processor. The featuring module 715 may be configured to perform one or more of the operations described above with respect to the featuring modules 325, 365 and the flowcharts of FIGS. 4-5. The labeling module 720 may be configured to perform one or more of the operations described above with respect to the labeling module 360 and the flowcharts of FIGS. 4-5. The storage policy recommendation engine 725 may comprise a machine learning engine module 730 and an AI engine module 735. The machine learning engine module 730 may be configured to perform one or more operations described above with respect to the machine learning engine 340 and the flowcharts of FIGS. 4-5. The AI engine module 735 may be configured to perform one or more operations described above with respect to the AI engine 345 and the flowcharts of FIGS. 4-5. The communication module 1240 may be configured to support communication between, for example, the AI server 140 and the health care facility interface server 130 and/or providers 110a, 110b, and 110c.

Although FIGS. 6-7 illustrate hardware/software architectures that may be used in data processing systems, such as the AI server 140 of FIG. 1 and the data processing system 600 of FIG. 6, respectively, in accordance with some embodiments of the inventive concept, it will be understood that embodiments of the present invention are not limited to such a configuration but is intended to encompass any configuration capable of carrying out operations described herein.

Computer program code for carrying out operations of data processing systems discussed above with respect to FIGS. 1-7 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the AI server 140 of FIG. 1 and the data processing system 600 of FIG. 6 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system."

The data processing apparatus described herein with respect to FIGS. 1-7 may be used to facilitate AI assisted data storage policy selection according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 705 when coupled to a processor includes computer readable program code that, when executed by the processor, causes the processor to perform operations including one or more of the operations described herein with respect to FIGS. 1-5.

Some embodiments of the inventive concept described herein may provide an AI assisted data storage policy selection system that is capable of learning which data storage policy is preferred for storing the data items for a particular entity, such as image data items associated with a patient in a health care environment. The AI assisted data storage policy selection system may seek to improve the KPI of the provider's facility, which is a sum of the cost of data storage and the cost of data retrieval. Modeling techniques, such as the multi-arm bandit algorithm, can be used to establish a baseline for the distribution of storage policies used for the different entities or patients. The system may then learn in real-time as new data storage requests are made so that the system may adapt to changes in the way data is used at a facility. In this way, broken or inapplicable data storage policies may be avoided so that they can be removed or revised. The system may also supplement its information foundation for making a data storage policy recommendation through additional information about an entity or patient, such as demographic information. This information may likewise be featured and modeled through application of one or more modeling techniques to improve the KPI of storage policy selection or recommendation.

Further Definitions and Embodiments:

In the above description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A method, comprising:
    defining a plurality of data storage policies, each of the plurality of data storage policies providing rules for storing data among a plurality of data storage locations, each of the plurality of data storage locations having a data storage cost and a data retrieval cost associated therewith;
    determining a baseline policy distribution among the plurality of data storage policies for an entity;
    receiving new data items corresponding to the entity;
    storing the new data items in the plurality of data storage locations using the plurality of data storage policies based on the baseline policy distribution; and
    determining, using an artificial intelligence engine, a selected one of the plurality of data storage policies to use in storing the new data items corresponding to the entity based on the data storage cost for each of the plurality of data storage locations and the data retrieval cost for each of the plurality of data storage locations;
    wherein a sum of the data storage costs and the data retrieval costs for the plurality of data storage locations associated with the selected one of the plurality of data storage policies is less than or equal to a sum of the data storage costs and the data retrieval costs for the plurality of data storage locations associated with other ones of the plurality of data storage policies, respectively.

2. The method of claim 1, wherein the method further comprises:
    evaluating a new data item storage metric for the new data items; and
    wherein determining, using the artificial intelligence engine, a selected one of the plurality of data storage policies to use in storing the new data items corresponding to the entity comprises:
    determining, using the artificial intelligence engine, a selected one of the plurality of data storage policies to use in storing the new data items corresponding to the entity based on the new data item storage metric, the data storage cost for each of the plurality of data storage locations, and the data retrieval cost for each of the plurality of data storage locations.

3. The method of claim 2, wherein evaluating the new data item storage metric for the new data items comprises:
    determining frequency of access for the new data items from the plurality of data storage locations.

4. The method of claim 1, wherein the baseline policy distribution among the plurality of data storage policies for the entity is a uniform policy distribution among the plurality of data storage policies.

5. The method of claim 1, wherein determining the baseline policy distribution among the plurality of data storage policies for the entity comprises:
    determining a historical distribution of the plurality of data storage policies for storing historical data items corresponding to the entity.

6. The method of claim 5, wherein determining the historical distribution of the plurality of storage policies for storing historical data items corresponding to the entity comprises:
    assigning the historical data items to ones of the plurality of data storage policies using a multi-arm bandit allocation process based on the data storage cost for each of the plurality of data storage locations and the data retrieval cost for each of the plurality of data storage locations.

7. The method of claim 1, wherein the entity is a patient and the new data items comprise new health care data items, the method further comprising:
receiving information associated with the patient; and
identifying features in the information associated with the patient that are predictive of a frequency of access for the new data items.

8. The method of claim 7, further comprising:
receiving labels for the information associated with the patient, the labels corresponding to frequency of access categories for the new data items.

9. The method of claim 8, wherein identifying the features in the information associated with the patient comprises:
identifying the features by applying a clustering technique to the information associated with the patient; or
identifying the features by applying a stepwise regression technique to the information associated with the patient.

10. The method of claim 9, wherein determining, using the artificial intelligence engine, the selected one of the plurality of data storage policies to use in storing the new data items corresponding to the patient comprises:
determining, using the artificial intelligence engine, the selected one of the plurality of data storage policies to use in storing the new data items corresponding to the patient by applying a modeling technique to the features in the information associated with the patient and the labels received for the information associated with the patient.

11. The method of claim 10, wherein the modeling technique comprises a multi-arm bandit technique a regression technique, a neural network technique, an Autoregressive Integrated Moving Average (ARIMA) technique, a deep learning technique, a linear discriminant analysis technique, a decision tree technique, a naïve Bayes technique, a K-nearest neighbors technique, a learning vector quantization technique, a support vector machine technique, and/or a bagging/random forest technique.

12. The method of claim 7, wherein the information associated with the patient comprises an age, a gender, a problem list, an encounter diagnosis, a patient class, and/or a medical center department.

13. The method of claim 1, wherein the plurality of data storage locations comprises an online storage location, a nearline storage location, and a coldline storage location.

14. A system, comprising:
a processor; and
a memory coupled to the processor and comprising computer readable program code embodied in the memory that is executable by the processor to perform operations comprising:
defining a plurality of data storage policies, each of the plurality of data storage policies providing rules for storing data among a plurality of data storage locations, each of the plurality of data storage locations having a data storage cost and a data retrieval cost associated therewith;
determining a baseline policy distribution among the plurality of data storage policies for an entity;
receiving new data items corresponding to the entity;
storing the new data items in the plurality of data storage locations using the plurality of data storage policies based on the baseline policy distribution; and
determining, using an artificial intelligence engine, a selected one of the plurality of data storage policies to use in storing the new data items corresponding to the entity based on the data storage cost for each of the plurality of data storage locations, and the data retrieval cost for each of the plurality of data storage locations;
wherein a sum of the data storage costs and the data retrieval costs for the plurality of data storage locations associated with the selected one of the plurality of data storage policies is less than or equal to a sum of the data storage costs and the data retrieval costs for the plurality of data storage locations associated with other ones of the plurality of data storage policies, respectively.

15. The system of claim 14, wherein the entity is a patient and the new data items comprise new health care data items, the operations further comprising:
receiving information associated with the patient; and
identifying features in the information associated with the patient that are predictive of a frequency of access for the new data items.

16. The system of claim 15, the operations further comprising:
receiving labels for the information associated with the patient, the labels corresponding to frequency of access categories for the new data items.

17. The system of claim 15, wherein identifying the features in the information associated with the patient comprises:
identifying the features by applying a clustering technique to the information associated with the patient; or
identifying the features by applying a stepwise regression technique to the information associated with the patient.

18. A computer program product, comprising:
a non-transitory computer readable storage medium comprising computer readable program code embodied in the medium that is executable by a processor to perform operations comprising:
defining a plurality of data storage policies, each of the plurality of data storage policies providing rules for storing data among a plurality of data storage locations, each of the plurality of data storage locations having a data storage cost and a data retrieval cost associated therewith;
determining a baseline policy distribution among the plurality of data storage policies for an entity;
receiving new data items corresponding to the entity;
storing the new data items in the plurality of data storage locations using the plurality of data storage policies based on the baseline policy distribution; and
determining, using an artificial intelligence engine, a selected one of the plurality of data storage policies to use in storing the new data items corresponding to the entity based on the data storage cost for each of the plurality of data storage locations, and the data retrieval cost for each of the plurality of data storage locations;
wherein a sum of the data storage costs and the data retrieval costs for the plurality of data storage locations associated with the selected one of the plurality of data storage policies is less than or equal to a sum of the data storage costs and the data retrieval costs for the plurality of data storage locations associated with other ones of the plurality of data storage policies, respectively.

19. The computer program product of claim 18, wherein the entity is a patient and the new data items comprise new health care data items, the operations further comprising:
    receiving information associated with the patient; and
    identifying features in the information associated with the patient that are predictive of a frequency of access for the new data items.

20. The computer program product of claim 19, the operations further comprising:
    receiving labels for the information associated with the patient, the labels corresponding to frequency of access categories for the new data items.

\* \* \* \* \*